United States Patent
Webb

[19]

[11] Patent Number: 6,082,362
[45] Date of Patent: *Jul. 4, 2000

[54] PUNCTUM PLUG

[75] Inventor: Nicholas J. Webb, Wrightwood, Calif.

[73] Assignee: Eagle Vision, Inc., Memphis, Tenn.

[ * ] Notice: This patent is subject to a terminal disclaimer.

[21] Appl. No.: 09/305,599

[22] Filed: May 5, 1999

Related U.S. Application Data

[63] Continuation-in-part of application No. 08/826,216, Mar. 27, 1997.

[51] Int. Cl.$^7$ .................................................. A61F 13/00
[52] U.S. Cl. .................................................. 128/846; 604/8
[58] Field of Search ................................ 604/4, 8, 9, 10, 604/54; 623/4; 127/887; 606/192

[56] References Cited

U.S. PATENT DOCUMENTS

| | | | |
|---|---|---|---|
| 2,487,038 | 11/1949 | Baum | 600/599 |
| 3,949,750 | 4/1976 | Freeman | 128/260 |
| 4,056,496 | 11/1977 | Mancini et al. | 260/29.6 |
| 4,660,546 | 4/1987 | Herrick et al. | 128/1 R |
| 4,886,488 | 12/1989 | White | 604/9 |
| 4,915,684 | 4/1990 | MacKeen | 604/8 |
| 4,959,048 | 9/1990 | Seder et al. | 604/9 |
| 5,049,142 | 9/1991 | Herrick et al. | 605/294 |
| 5,171,270 | 12/1992 | Herrick | 623/11 |
| 5,283,063 | 2/1994 | Freeman | 424/427 |
| 5,318,513 | 6/1994 | Leib | 604/8 |
| 5,334,137 | 8/1994 | Freeman | 604/8 |
| 5,417,651 | 5/1995 | Guena et al. | 604/8 |
| 5,423,777 | 6/1995 | Tajiri et al. | 604/294 |
| 5,522,837 | 6/1996 | Latina | 606/201 |
| 5,601,553 | 2/1997 | Trebing et al. | 606/61 |
| 5,626,559 | 5/1997 | Solomon | 604/9 |
| 5,645,565 | 7/1997 | Rudd et al. | 606/213 |
| 5,723,005 | 3/1998 | Herrick | 623/4 |
| 5,766,243 | 6/1998 | Christensen | 623/4 |
| 5,830,171 | 11/1998 | Wallace | 604/8 |

*Primary Examiner*—Michael A. Brown
*Attorney, Agent, or Firm*—David P. Gordon; David S. Jacoboson; Thomas A. Gallagher

[57] ABSTRACT

A punctum plug includes a proximal head, a distal body, and a thin-walled flexible shaft between the head and the body. The thin wall of the shaft of the plug is preferably provided with accordion-like folds, thereby permitting the length of the shaft to vary depending upon the degree to which the accordion-like folds are folded or unfolded. In addition, the accordion-like folds permit the thin wall of the shaft to easily bend, permitting the head and body of the plug to lie along different axes. As a result, the plug is shaped to accommodate both relatively long and short vertical puncta and the body of the plug may be angled relative to the head to accommodate a variety of anatomical structures. According to another aspect of the invention, the body of the plug may be provided with a thread which rotationally guides the plug into the small punctal opening when insertional and rotational forces are applied to the plug. As a result, a relatively larger body size may be used. Moreover, the thread provides improved plug fixation.

20 Claims, 5 Drawing Sheets

PUNCTUM PLUG

This application is a continuation-in-part of U.S. Ser. No. 08/826,216, filed Mar. 27, 1997, which is hereby incorporated by reference herein in its entirety.

BACKGROUND OF THE INVENTION

1. Field of the Invention

This invention relates broadly to medical canalicular inserts. More particularly, this invention relates to plugs which are placed into the punctal opening of the lacrimal duct to prevent lacrimal fluid from flowing through the lacrimal duct.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctual opening have been used to prevent drainage of tears through the nasal lacrimal duct, including suturing, laser sealing, and plugging. Plugging with a punctum plug is the least severe solution, is relatively inexpensive, and is being performed with increasing frequency.

Referring to prior art FIG. 1, a punctum plug 10 typically is an elongate member having a proximal head 12, a large distal body 14 for occluding the lacrimal duct 16, and a narrow rigid shaft 18 therebetween. The plug is usually provided with a proximal axial conduit 20 for receiving an cylindrical insertion tool. In the punctum plug insertion procedure, an insertion tool is positioned into the plug, the body of the plug is directed at the punctal opening 22 of the lacrimal duct 16, and force is applied to the insertion tool to move the body of the plug through the punctal opening and into the vertical puncta 24 and lacrimal duct 16. Once the plug is in the vertical puncta and lacrimal duct, the insertion tool is removed. The plug is fully inserted when the head seats against the tissue at the punctal opening and the body seats within the lacrimal duct so as to block the passage of tear fluid and thereby retain tear fluid at the surface of the eye.

It has been found that prior art punctum plugs, while providing some benefit often do not provide satisfactory occlusion of the lacrimal duct. Tear fluid tends to flow through the interstices between the body of the plug and the tissue of the vertical puncta of the nasal lacrimal duct. One proposed prior art solution of this problem has been to provide an enlarged distal body to the plug. However, this poses two problems. First, the larger distal body is difficult to insert into the relatively small punctal opening. Second, some persons have relatively short vertical puncta. As a result, the body of the plug, rather than resting within the vertical puncta, is forced against the duct tissue 26 where the vertical puncta meets the lacrimal duct. This urges the plug upwards and can cause the plug to be unintentionally dislodged.

Another problem of the prior art plugs is that, in some instances, the plugs cannot be easily extricated from the punctum. Occasionally, the tissue of the vertical puncta closes in around the shaft of the plug. As a result, when lifting force is applied to the head of a well-seated plug to lift the plug out of the puncta, the plug tends to break at the shaft. The plug is thereby decapitated leaving the body and a portion of the shaft behind, which cannot be removed without a more severely invasive procedure.

SUMMARY OF THE INVENTION

It is therefore an object of the invention to provide a punctum plug which fully blocks tears from flowing into the punctal opening of the nasal lacrimal duct.

It is another object of the invention to provide a punctum plug which is not easily unintentionally removed from the puncta.

It is a further object of the invention to provide a punctum plug which can easily be extricated by a physician when desired.

It is also an object of the invention to provide a punctum plug which adjusts to the length of the vertical puncta of the individual into which the plug is inserted.

In accord with these objects which will be discussed in detail below, a punctum plug is provided generally having a proximal head, a distal body, and a thin-walled flexible shaft between the head and the body. According to one preferred embodiment of the invention, the thin wall of the shaft of the plug has preformed folds, preferably accordion-like, thereby permitting the length of the shaft to vary depending upon the degree to which the folds are folded or unfolded. As a result, the plug is shaped to accommodate both relatively long and short vertical puncta. In addition, the tissue forming the punctum may enter into the folds such that a relatively high level of surface contact exists between the plug and the tissue. This relatively large surface contact provides enhanced fixation of the plug in the punctum. Moreover, the folds permit the thin wall of the shaft to easily bend, permitting the head and body of the plug to lie along different axes, particularly useful in persons having short vertical puncta. In addition, the body of the plug may be angled relative to the head to accommodate a variety of anatomical structures. Other embodiments provide for circumferential grooves or structural ribs which likewise permit the shaft to easily bend. According to another preferred aspect of the invention, the body of the plug is preferably provided with an external thread. Alteratively, and according to yet another embodiment of the invention, the body of the plug is provided with a spiralled groove. It will be appreciated that both of the thread and the groove are capable of rotationally guiding the plug into the small punctal opening when insertional and rotational forces are applied to the plug. As a result, a relatively larger body size may be used. Moreover, both the thread and the groove provide improved plug fixation. Furthermore, the head of the plug is preferably concave, thereby minimizing the potential for corneal contact with the head. In addition, the body of the plug is preferably pointed, allowing easier insertion into the punctal opening, but may alternatively be truncated or rounded.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
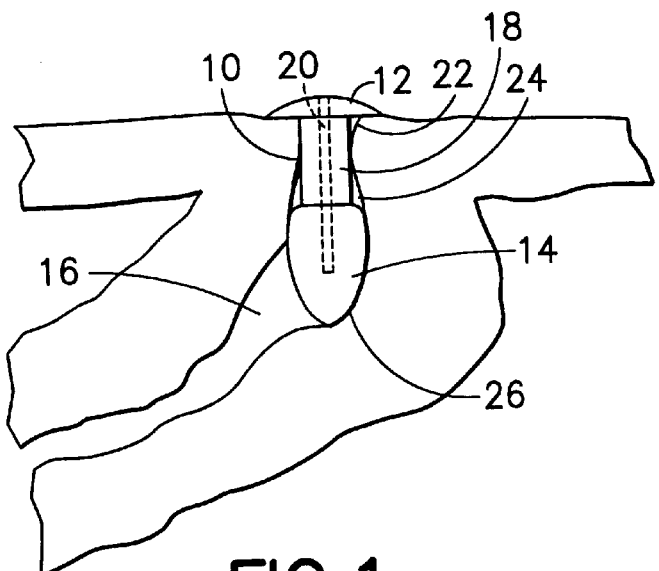
FIG. 1 is a side elevation of an implanted prior art punctum plug.
Figure 2:
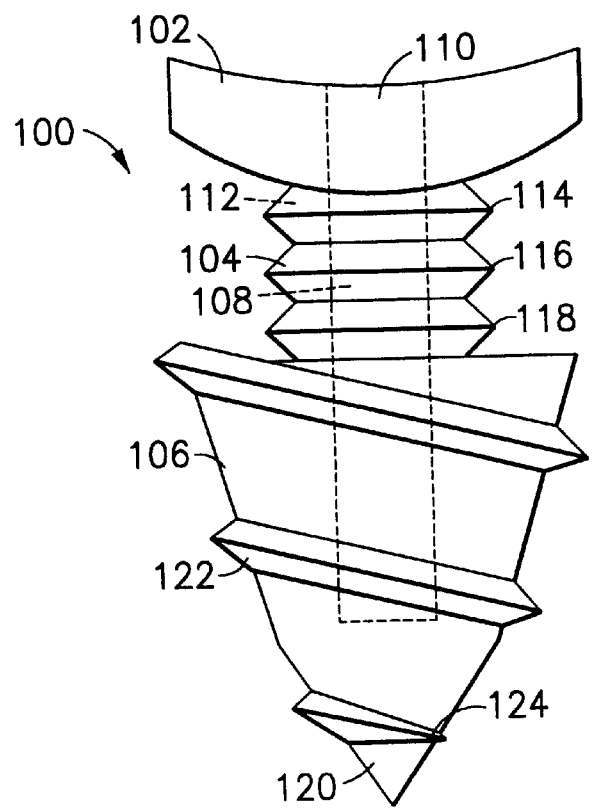
FIG. 2 is a side elevation of a punctum plug according to a first embodiment of the invention.
Figure 3:
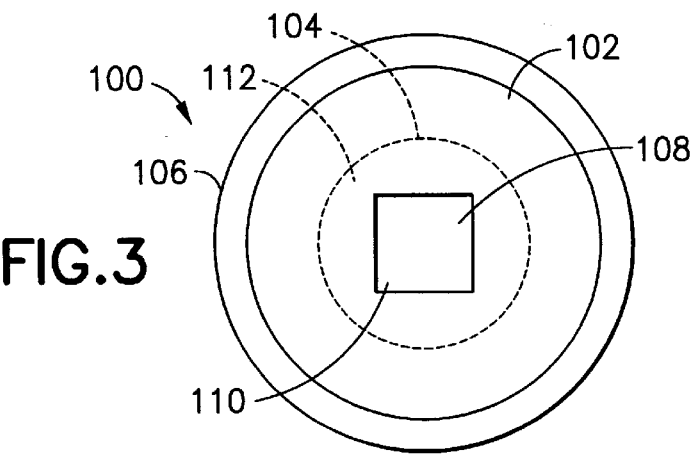
FIG. 3 is a top view of a punctum plug according to the first embodiment of the invention.

Turning now to FIG. 2, a first and presently preferred embodiment of a punctum plug 100 according to the invention is shown. The punctum plug 100 generally includes a head 102, a shaft 104 and a body 106. An axial bore 108 is provided through the head 102 and shaft 104 and into the body 106. The axial bore 108 preferably has a non-circular cross-sectional shape. Referring to FIG. 3, a top view of the plug- shows an axial bore having a rectangular cross-section. Preferably, the plug is made from silicone or another soft, low durometer material, by liquid injection molding, cast molding, or transfer molding.

Turning back to FIG. 2, the head 102 of the plug preferably has a concave proximal surface 103. Preferably, the shaft 104 includes a relatively thin wall 112 surrounding the axial bore 108. The thin wall 112 permits the shaft 104 to flex. Preferably the wall 112 of the shaft is provided with a plurality of folds 114, 116, 118, preferably accordion-like. The thin wall preferably has an average thickness approximately one-fourth the diameter of the shaft. The body 106 of the plug is substantially conical, and preferably has a pointed tip 120. A thread 122 is preferably provided on the body, spiraling around the body from the upper to tip portions of the body. The thread 122 preferably includes a tapered portion 124 near the tip 120 of the body 106.

It will be appreciated that the first embodiment of the punctum plug provides several advantages over prior art punctum plugs. The folds permit the length of the shaft to vary depending upon the degree to which the folds are folded or unfolded. In addition, the folds permit the thin wall of the shaft to easily bend, permitting the head and body of the plug to lie along different axes. As a result, the plug is shaped to accommodate both relatively long and short vertical puncta and the body may be angled relative to the head to accommodate a variety of anatomical structures. Moreover, the concave design of the head minimizes the potential for corneal contact with the plug. Furthermore, the point at the tip of the body enables easier insertion of the plug into the punctal opening and the thread rotationally guides the plug into the puncta. In addition, the thread grabs into the tissue of the puncta and provides improved plug fixation.

Plugs may be provided in several sizes to provide satisfactory insertion into puncta of varying dimensions and to thereby occlude nasal lacrimal duct. By way of example, and not by way of any limitation, the following dimensions are provided for one size of the first embodiment of the punctum plug. The plug 100 has a length of approximately 0.065 inches from head 102 to tip 120. The head has a diameter of approximately 0.040 inches. The shaft has a diameter of approximately 0.020 inches. The length of the plug from the proximal end of the head to the location where the shaft meets the body is approximately 0.025 inches. The thread rises approximately 0.005 inches form the body and the width of the thread is approximately 0.005 inches.

Figure 4:
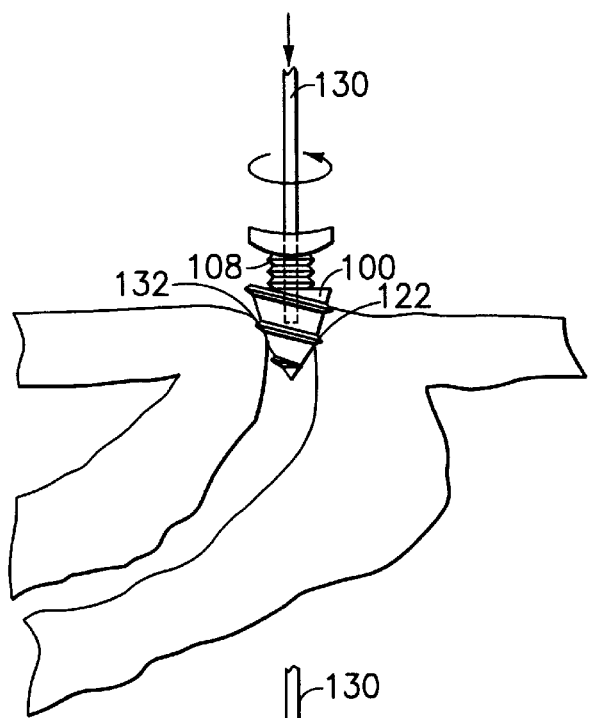
FIGS. 4 through 6 illustrate the method according to the invention of inserting the punctum plug of FIG. 2.
Figure 5:
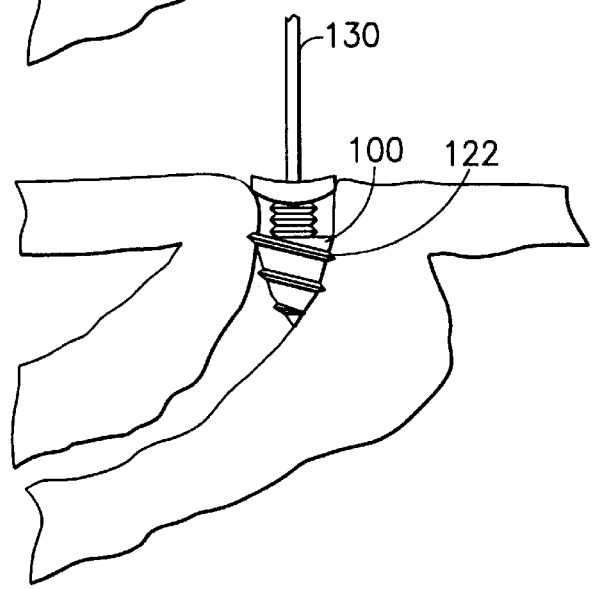
Figure 6:
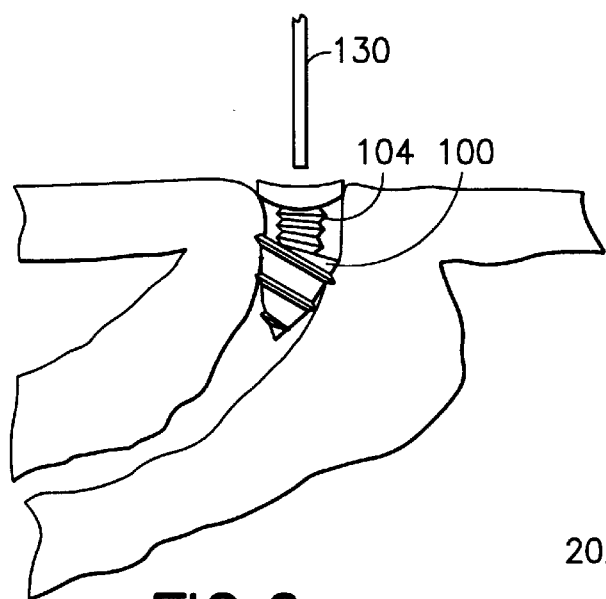

Referring to FIGS. 4 through 6, the plug 100 is inserted as follows into the puncta to block the flow of tears through the nasal lacrimal duct. Particularly with reference to FIG. 4, an insertion tool 130 having substantially the same non-circular cross-section as provided to the axial bore is seated in the axial bore 108 of the plug 100, thereby providing rigidity to the plug. The body of the plug is brought to the punctal opening 132. The insertion tool is rotated and pressure is applied to slowly force the plug into the punctal opening. Rotation of the insertion tool rotates the plug and causes the thread 122 to grab into the tissue of the puncta and to guide the plug further into the puncta. Referring to FIG. 5, the plug is inserted in this manner until the head seats substantially flush around the punctal opening. Referring to FIG. 6, once the plug is inserted, the insertion tool is removed thereby allowing the shaft of the plug to flex. The plug flexes around the shaft 104 to conform to the anatomical shape of the puncta, particularly to the length (with the accordion-like folds flexed as shown in FIG. 6).

Figure 7:
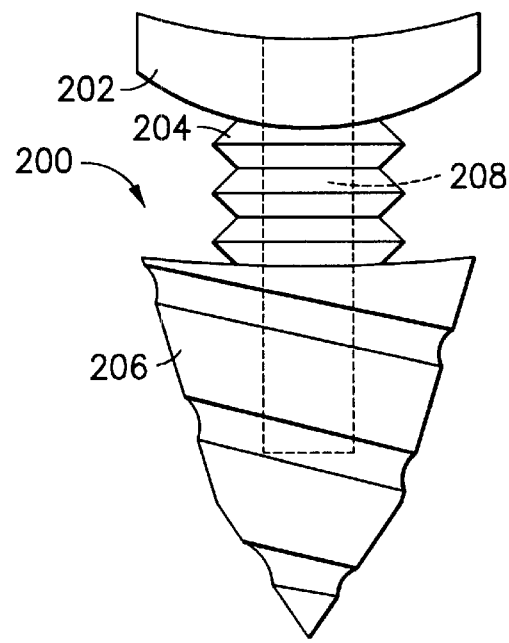
FIG. 7 is a side elevation of a punctum plug according to the second embodiment of the invention.
Figure 8:
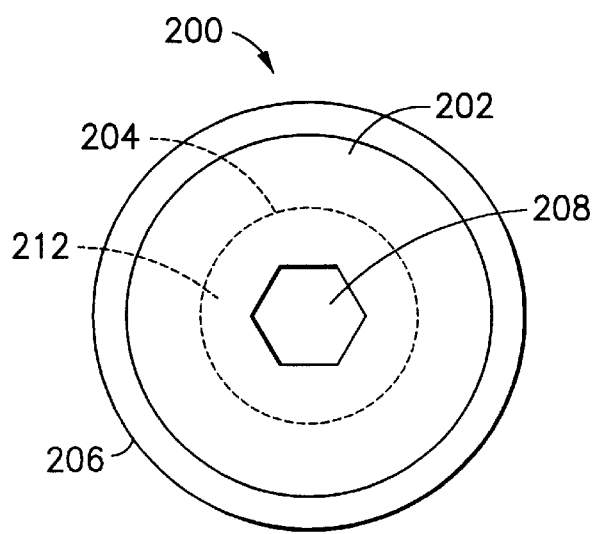
FIG. 8 is a top view of a punctum plug according to a second embodiment of the invention.

Referring now to FIG. 7, a second embodiment of a punctum plug 200, substantially similar the punctum plug of the first embodiment (with like parts having similar numbers incremented by 100), is shown. The plug 200 includes a head 202, a preferably flexible shaft 204, and a body 206. An axial bore 208, preferably having a non-circular cross-section, is provided through the head 202 and shaft 204 and into the body 206. The shaft may be shaped to have an axial bore having a hexagonal cross-section (see FIG. 8), a rectangular cross-section (as shown in FIG. 3), or another cross-section. The wall 212 of the shaft 206 is preferably provided with folds. A spiral groove 222 (or broad thread) is provided on the body for guiding the plug into the puncta.

Figure 9:
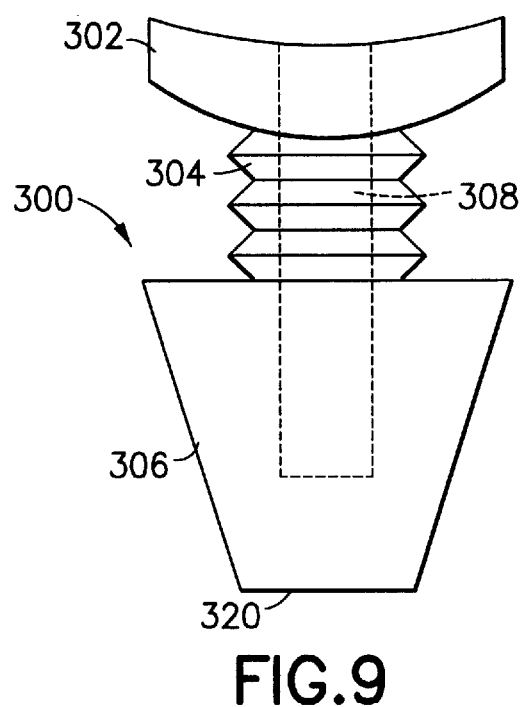
FIG. 9 is a side elevation of a punctum plug according to a third embodiment of the invention.
Figure 10:
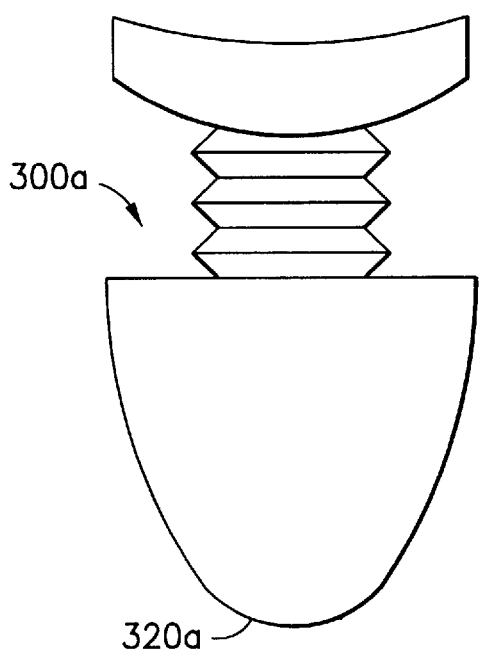
FIG. 10 is a side elevation of a punctum plug according to a fourth embodiment of the invention.

Turning now to FIG. 9, a third embodiment of a punctum plug 300 according to the invention, substantially similar to the first embodiment (with like parts having numbers incremented by 200), is shown. The punctum plug 300 includes a head 302, a shaft 304, and a body 306. An axial bore 308, preferably having a non-circular cross-section, is provided through the head and shaft and into the body. The head preferably has a concave design. The shaft has a thin wall which preferably has folds. The body preferably has a truncated distal end 320, but may also have a pointed distal end, as described above; or according to a fourth embodiment of a plug 300a, shown in FIG. 10, may have a rounded distal end 320a.

Figure 11:
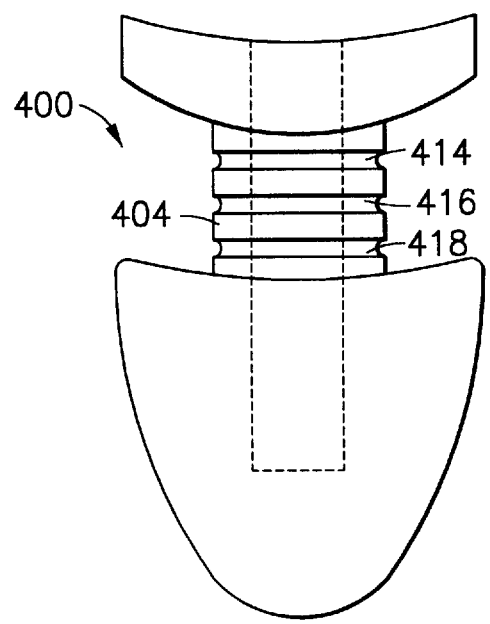
FIG. 11 is a side elevation of a punctum plug according to a fifth embodiment of the invention.

Referring to FIG. 11, a fifth embodiment of a punctum plug 400 according to the invention, substantially similar to the first embodiment (with like parts having numbers incremented by 300), is shown. The shaft 404 of the punctum plug 400 has a plurality of substantially circumferential grooves 414, 416, 418 which facilitate the easy bending of the shaft to allow the plug to accommodate a variety of anatomical configurations.

Figure 12:
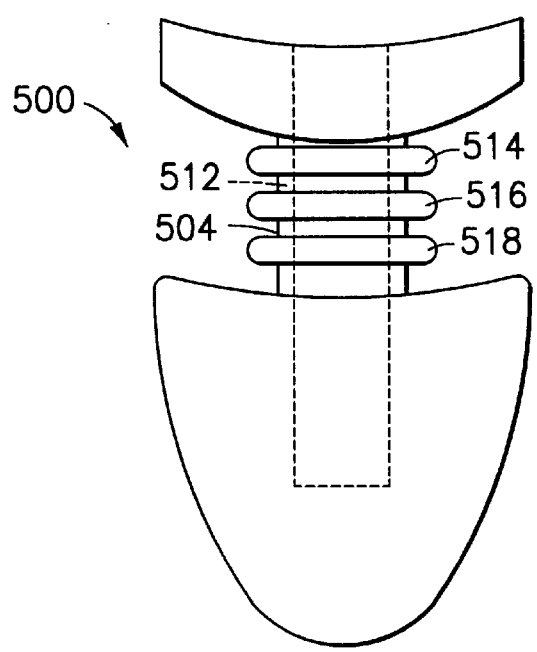
FIG. 12 is a side elevation of a punctum plug according to a sixth embodiment of the invention.

Turning to FIG. 12, a sixth embodiment of a punctum plug 500 according to the invention, substantially similar to the first embodiment (with like parts having numbers incremented by 400), is shown. The shaft 504 of the punctum plug 500 has a plurality of structural ribs 514, 516, 518. The shaft bends easily at the thin wall 512 between the ribs allowing the plug to accommodate a variety of anatomical configurations. In addition, providing ribs 514, 516, 518 to a low durometer material plug 500 permits the shaft 504 to bend or axially change length in an accordion-like manner along the shaft at the material between the ribs.

Figure 13:
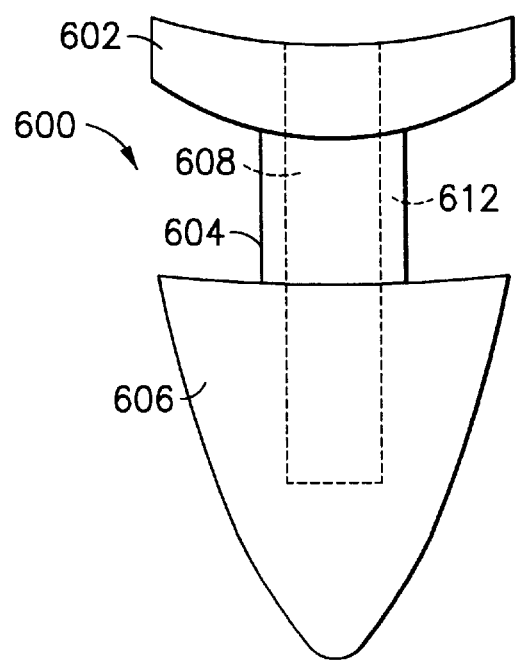
FIG. 13 is a side elevation of a punctum plug according to a seventh embodiment of the invention.

Referring to FIG. 13, a seventh embodiment of a punctum plug 600 according to the invention, substantially similar to the first embodiment (with like parts having numbers incremented by 500), is shown. The punctum plug 600 includes a head 602, a shaft 604, and a body 606. An axial bore 608, preferably having a non-circular cross-section, is provided through the head 602 and the shaft 604 and into the body 606. The shaft 604 preferably has a smooth surface and a flexible wall 612 surrounding the axial bore 608. The wall 612 preferably has a thickness approximately one-fourth the diameter of the shaft.

There have been described and illustrated herein several embodiments of a punctum plug and a method of inserting a punctum plug into the puncta to occlude the nasal lacrimal duct. While particular embodiments of the invention have been described, it is not intended that the invention be limited thereto, as it is intended that the invention be as broad in scope as the art will allow and that the specification be read likewise. Thus, while the head has been disclosed as preferably being concave, it will be appreciated that a flat head or a dome-like head can also be used. In addition, while an accordion-like shaft design is preferred for the embodiments incorporating a threaded or grooved body, it will be recognized that a relatively smooth shaft, grooved shaft, or ribbed shaft may also be used in combination with a threaded or grooved body. Furthermore, while the shaft has been shown to include folds, grooves, ribs, and/or a thin wall to facilitate bending, it will be appreciated that other structural design may alternatively or additionally be provided on the shaft to facilitate bending. Moreover, while it is preferable that the shaft be flexible, it will be understood that the shaft need not be flexible. Furthermore, while particular shapes for the body of the plug have been disclosed with respect to certain embodiments, it will be appreciated that other shapes may be used as well, particularly those disclosed for other embodiments. For example, and not by way of limitation, each of the embodiments may have a pointed, rounded or truncated tip. Moreover, the shaft has been described to define an axial bore, preferably having a non-circular cross-section. While a rectangular or hexagonal cross-section has been described as preferred with particular embodiments, in each of the embodiments a rectangular or hexagonal cross-section may be provided to the bore, a different non-circular cross-section may be provided to the bore, or a circular cross-section may be provided to the bore. Also, the axial bore may be confined to the head and shaft (and not enter the body) or may enter further or less into the body than illustrated in the Figures. In addition, while the plug has been described as preferably being made from silicone, it will be appreciated that other suitable materials known to those skilled in the art may also be used. Furthermore, different parts of the plug can be made from different materials. Moreover, while the methods of liquid injection molding, cast molding, and transfer molding are disclosed for making the plugs, other methods known in the art can also be used. It will therefore be appreciated by those skilled in the art that yet other modifications could be made to the provided invention without deviating from its spirit and scope as so claimed.

We claim:

1. A punctum plug for insertion into a punctal opening of a nasal lacrimal duct and adapted for use with an insertion tool having a non-circular cross-section, said punctum plug comprising:
    a) a proximal head portion;
    b) a distal body portion sized to fit into the punctal opening;
    c) a shaft portion between said head portion and said body portion,
       said head portion and said shaft portion at least partially defining an axial bore having a non-circular cross-section, said axial bore for cooperating with the insertion tool.

2. A punctum plug according to claim 1, wherein:
   said head portion, said shaft portion, and said body portion defining said axial bore, said axial bore having one of a rectangular and hexagonal cross-section.

3. A punctum plug according to claim 1, wherein:
   said head portion has a concave proximal surface.

4. A punctum plug according to claim 1, wherein:
   said distal body portion has a thread.

5. A punctum plug according to claim 1, wherein:
   said shaft portion is flexible.

6. A punctum plug according to claim 5, wherein:
   said shaft portion has a diameter and includes a wall having a thickness approximately one-fourth said diameter of said shaft portion.

7. A punctum plug according to claim 5, wherein:
   said shaft portion has a circumference and includes at least one of a foldable portion, a groove, and a rib substantially around said circumference and about which said shaft portion is adapted to flex.

8. A punctum plug according to claim 1, wherein:
   said body portion includes a tip which is one of pointed, rounded and truncated in shape.

9. A punctum plug for insertion into a punctal opening of a nasal lacrimal duct, said punctum plug comprising:
    a) a proximal head portion;
    b) a distal body portion sized to snugly fit into the punctal opening; and
    c) a shaft portion having a circumference and at least one of a foldable portion, a groove, and a rib substantially around said circumference and about which said shaft portion is adapted to flex.

10. A punctum plug according to claim 9, wherein:
    said head portion has a concave proximal shape.

11. A punctum plug according to claim 9, wherein:
    said body portion includes a tip which is one of pointed, rounded and truncated in shape.

12. A punctum plug according to claim 9, wherein:
    said body portion has a thread.

13. A punctum plug according to claim 12, wherein:
    said thread is an external thread having a width of approximately 0.005 inches.

14. A punctum plug according to claim 12, wherein:
    said thread is an external thread which is raised from said body by approximately 0.005 inches.

15. A punctum plug for insertion into a punctal opening of a nasal lacrimal duct, said punctum plug consisting essentially of:
    a) a proximal head portion;
    b) a distal body portion sized to fit into the punctal opening such that the lacrimal duct is occluded, said body portion having an outer surface with a spiraling means for guiding said punctum plug into the punctal opening, said spiraling means sized to engage the punctal opening; and c) a shaft portion between said head portion and said body portion.

16. A punctum plug according to claim 15, wherein:
said means for guiding is a thread.

17. A punctum plug according to claim 15, wherein:
said shaft portion includes a circumference and at least one of a foldable portion, a groove, and a rib substantially around said circumference about which said shaft portion is adapted to flex.

18. A punctum plug according to claim 15, wherein:
said body portion is substantially conically shaped.

19. A punctum plug according to claim 15, wherein:
said head portion has a concave proximal surface.

20. A method of inserting a punctum plug into the punctal opening of the nasal lacrimal duct, the punctum plug having head, shaft, and body portions which define an axial bore having a substantially non-circular cross-section, said method comprising:

a) inserting an insertion tool having a substantially non-circular cross-section into the axial bore of the punctum plug such that rotation of the insertion tool causes the punctum plug to rotate;

b) positioning the body portion of the plug against the punctal opening of the nasal lacrimal duct;

c) applying rotational and insertional force to the insertion tool until the punctum plug is satisfactorily inserted into the nasal lacrimal duct; and d) removing the insertion tool.

* * * * *